United States Patent
McEwen et al.

(10) Patent No.: US 6,746,470 B2
(45) Date of Patent: Jun. 8, 2004

(54) EMERGENCY AND MILITARY TOURNIQUET FOR PRE-HOSPITAL USE

(76) Inventors: James Allen McEwen, 10551 Bamberton Drive, Richmond, B.C. (CA), V7A 1K6; Kevin Bryant Inkpen, 1950 Graveley Street, Vancouver, B.C. (CA), V5L 3B4; Kenneth L. Glinz, #20-7651 Francis Rd., Richmond, B.C. (CA), V6Y 1A3; Michael Jameson, 2365 Badger Rd., North Vancouver, B.C. (CA), V7G 1S9

(*) Notice: Subject to any disclaimer, the term of this patent is extended or adjusted under 35 U.S.C. 154(b) by 317 days.

(21) Appl. No.: 10/053,813

(22) Filed: Jan. 18, 2002

(65) Prior Publication Data

US 2003/0139766 A1 Jul. 24, 2003

(51) Int. Cl.[7] ................................. A61B 17/00
(52) U.S. Cl. ..................................... 606/202
(58) Field of Search ............................. 606/201, 202, 606/203; 600/490, 499; 128/96.1, 118.1

(56) References Cited

U.S. PATENT DOCUMENTS

| | | | |
|---|---|---|---|
| 4,211,289 A | * | 7/1980 | Klein .................... 606/202 |
| 4,243,039 A | | 1/1981 | Aginsky |
| 4,441,504 A | * | 4/1984 | Peterson et al. ........... 606/202 |
| 4,466,437 A | * | 8/1984 | Dyck et al. ............... 606/201 |
| 4,469,099 A | | 9/1984 | McEwen |
| 4,479,494 A | | 10/1984 | McEwen |
| 4,605,010 A | | 8/1986 | McEwen |
| 4,727,885 A | | 3/1988 | Ruff |
| 4,770,175 A | | 9/1988 | McEwen |
| 4,869,265 A | | 9/1989 | McEwen |
| 5,048,536 A | | 9/1991 | McEwen |
| 5,181,522 A | | 1/1993 | McEwen |
| 5,312,431 A | | 5/1994 | McEwen |
| 5,314,437 A | | 5/1994 | Holtsch |
| 5,454,831 A | | 10/1995 | McEwen |
| 5,578,055 A | | 11/1996 | McEwen |
| 5,584,853 A | | 12/1996 | McEwen |
| 5,628,723 A | | 5/1997 | Grau |
| 5,649,954 A | | 7/1997 | McEwen |
| 5,741,295 A | | 4/1998 | McEwen |
| 5,855,589 A | | 1/1999 | McEwen |
| 5,911,735 A | | 6/1999 | McEwen |
| 5,931,853 A | | 8/1999 | McEwen |
| 5,935,146 A | | 8/1999 | McEwen |
| 6,149,666 A | | 11/2000 | Marsden |
| 6,213,939 B1 | | 4/2001 | McEwen |

OTHER PUBLICATIONS

Calkins, Snow, Costello, and Bentley; 'Evaluation of possible battlefield tourniquet systems for the far–forward setting', Military Medicine 165, 5:379 (vol. 165 May 2000 pp. 379–384).

* cited by examiner

Primary Examiner—Kevin T. Truong
(74) Attorney, Agent, or Firm—ipsolon LLP

(57) ABSTRACT

A pneumatic tourniquet adapted for self application by an injured person in a military or emergency situation to stop arterial blood loss in an injured arm or leg comprises: a bladder having a width dimension and having a length dimension greater than the circumference of an injured limb of a subject at a selected location; and clamp means for securing the bladder around the limb at the selected location and adapted for sealing the bladder across the bladder width to establish an inflatable portion of the bladder to be the portion of the bladder that encircles the injured limb at the selected location.

11 Claims, 6 Drawing Sheets

EMERGENCY AND MILITARY TOURNIQUET FOR PRE-HOSPITAL USE

BACKGROUND

Loss of blood is a major cause of death in military combat and emergency situations in which the injured person is alone or medical assistance is not immediately available. The use of a tourniquet to stop blood loss from an injured arm or leg is a well-known technique for preventing death in these situations. Once the primary objective of preventing death due to blood loss is achieved, it is desirable to prevent further injury to the limb due to excessive pressure and time of tourniquet application. To minimize mechanical injury to the tissues under the tourniquet, the pressure applied by the tourniquet should be only slightly higher than that required to stop blood flow and the pressure should be applied evenly and uniformly around the limb beneath the tourniquet, without localized regions of very high or very low pressures. To help prevent gangrene and other complications related to the lack of arterial blood flow into the portion of the limb distal to the tourniquet, it is widely accepted that the tourniquet pressure should be released for a period of 5–10 minutes and then reapplied after each two hour period of stoppage of arterial blood flow, also called arterial blood flow occlusion. When more sophisticated care becomes available (such as emergency medical personnel arriving at the scene or evacuation to a field hospital), it is advantageous to have the emergency tourniquet compatible with more sophisticated pneumatic tourniquet systems (such as the pneumatic systems described by McEwen in U.S. Pat. No. 4,469,099) which allow precise control of tourniquet cuff pressure and application time.

Published US Army research (Calkins et al, 'Evaluation of possible battlefield tourniquet systems for the far-forward setting', *Military Medicine Vol.* 165, 5:379, May 2000) defines the need for a light, compact, yet rugged tourniquet for far-forward battlefield use. The victim must be able to apply the tourniquet to his or her own arm or leg and occlude blood flow using only their non-dominant hand. In the Calkins study, a variety of prior art pneumatic and non-pneumatic tourniquets and other non-pneumatic devices adapted for use as a tourniquet (such as ratcheting cargo straps) were tested and found to have disadvantages or to be ineffective in occluding arterial blood flow, particularly when self-applied. Calkins et al reviewed issued patents and found no suitable devices disclosed.

In U.S. Pat. No. 4,243,039, Aginsky discloses an emergency tourniquet consisting of a strap and ratchet-type tensioning device, including a tension indicating device and a pointer intended to be set by the user to indicate the time of tourniquet application. In the Calkins study a similar ratchet type devices did not successfully occlude arterial blood flow in all cases and the noisy operation, pinching of the skin, and questionable durability of these types of device was criticized. The pointer device disclosed by Aginsky in the '039 patent requires the victim to set the pointers at the time of tightening the tourniquet and then monitor the current time using separate means to determine when to release the tourniquet. This is a disadvantage in the battlefield or emergency situation because the user, who may be injured and under extreme stress, must have a reliable separate means of measuring time, must remember to set the pointers immediately after tightening the tourniquet the limb, and must be alert enough to monitor the time throughout the maximum desirable period of continuous arterial occlusion.

There are many other non-pneumatic constricting devices (such as elastic and non-elastic straps) in the prior art. For example the emergency bandage described by Grau in U.S. Pat. No. 5,628,723 is intended to be wrapped tightly around the limb as a pressure dressing, but may be used as a tourniquet by using a windlass to twist the wrapped bandage and generate sufficient inward radial pressure on the limb to stop arterial blood flow. However the Calkins study showed that these types of devices were generally not capable of stopping arterial blood flow in the limb, particularly when self-applied by the victim. In U.S. Pat. No. 5,314,437, Holtsch describes a constricting device for body parts in which a non-inflating band encircles the body part. When the band is pulled tight, the resulting tension activates a rocker clamp which locks the band at a fixed circumference. Although this device may be easier to self-apply due to the automatic clamp, it is intended for venous occlusion only and it would be difficult or impossible for the victim to generate sufficient tension in the band to occlude arterial blood flow. In U.S. Pat. No. 6,149,666, Marsden describes a constricting strap and fastener device with a battery powered timer and alarm system activated by closure of the fasteners at one or more discrete circumferences. However this non-pneumatic device is a venous tourniquet to assist in various intravenous procedures and is not suitable for arterial occlusion.

Non-pneumatic strap type tourniquets such as those described above generate inward radial compression on the limb by being put into high levels of circumferential tension when wrapped around the limb. In ratcheting strap devices (such as that described by Aginsky in the '039 patent) and other strap and buckle type devices (such as that described by Holtsch in the '437 patent and the cargo strap device tested by Calkins), tension is generated by shortening the strap wrapped around the limb. As the pressure on the limb increases, the friction between the strap and the limb also increases, causing the underlying soft tissue to move with the strap as it is drawn tight. This tends to draw soft tissues underlying the strap into the ratchet or buckle device, pinching the soft tissue and creating a region of very high localized pressure which will cause unnecessary injury. This effect may also create high shearing stresses in the underlying soft tissues, increasing the probability of nerve and tissue injury. Friction between the strap and the limb may also create regions of low pressure by preventing tension from being distributed evenly in the strap around the entire limb circumference, and as a result arterial blood may still flow through these low pressure regions although overall strap tension is very high. In general, the uneven or non-uniform application of pressure around the limb resulting from the use of non-pneumatic strap type tourniquets leads to the need for unnecessarily high overall tourniquet pressures to reliably and predictably stop arterial blood flow, and this need for unnecessarily high pressure increases the probability of a range of unnecessary injuries to nerves, muscles and limb. Using a pressure transducer as described by McEwen in U.S. Pat. No. 4,869,265, the inventors of the current invention have found that pressure distribution under non-pneumatic strap type tourniquets is difficult to regulate and can vary significantly between different locations around the limb circumference and between the proximal and distal edges of the strap. In particular, pressures actually applied to the limb can be dangerously high in certain areas (such as the pinched areas described above) with corresponding increased risk of soft tissue and nerve damage. Areas of low pressure can allow arterial blood flow past the tourniquet and lead to higher overall strap tensions being used to maintain arterial occlusion. Furthermore, none of the non-pneumatic devices described above are compatible with typical operating room or field hospital tourniquet systems allowing precise control of tourniquet pressure.

Pneumatic tourniquet cuffs have been proven to be effective and safe devices for stopping arterial blood flow and are the standard of care in modern surgery. A pneumatic cuff was the only device tested that successfully stopped arterial blood flow in all trials in the Calkins study. When a pneumatic tourniquet cuff is in use, an inflatable bladder completely encircles the limb and is inflated, causing the bladder to expand and apply inward radial compression to the limb around the entire limb circumference. In contrast to the non-pneumatic devices described above, pneumatic tourniquets apply pressure to the limb that is very closely related to the inflation pressure of the cuff, and this pressure is applied evenly around the entire limb circumference. It is therefore easy to control the pressure applied to the limb by monitoring the cuff inflation pressure, and low pressure areas are minimized. Because the inward radial pressure on the limb is provided by the inflation pressure in the bladder rather than circumferential tension, the cuff does not need to be applied with great tension and the problems of pinching and shearing of the soft tissues (as described in the preceding paragraph) are minimized and self application is easier. A pneumatic tourniquet cuff must, however, be snugly applied around the limb and secured at a fixed circumference to be effective.

The pneumatic cuff tested in the Calkins study was similar to the overlapping occlusive cuffs for surgical use described by McEwen in U.S. Pat. Nos. 5,649,954 and 5,741,295. These cuffs consist of an inflatable bladder portion longer than the circumference of the largest limb expected to be occluded with the cuff, such that the bladder overlaps upon itself when wrapped around the limb. To help maintain an even pressure distribution around the limb and to reduce the likelihood of slippage of overlapping regions of the cuff along the limb, the amount of overlap in surgical tourniquet cuffs is generally limited to a range of roughly 1 to 5 inches, meaning that different cuff sizes are required to accommodate the arm and leg circumferences of different individuals. Overlapping pneumatic tourniquet cuffs are intended for use in the surgical setting where a source of compressed gas is available and the cuff is applied by a skilled technician. Typically the appropriate size of cuff is selected and wrapped around the limb and secured by hook and loop type fastening straps. The cuff is then inflated, and the full length of the bladder (both the portion contacting the limb and the overlapping portion) inflates. This type of cuff is undesirable in the battlefield or emergency situation because:

It is difficult to wrap these cuffs and close the fasteners with one hand (particularly on one's own limb), Hook and loop type fasteners can become unreliable when wet and fouled with dirt, The inflated volume of these overlapping cuffs is always large enough for the largest limb in the recommended size range, even when the cuff is applied to the smallest limb in the range. This is a disadvantage when the user must inflate the cuff quickly with a manual pump, and The limb size range of these overlapping cuffs is typically too narrow for a single cuff type to be applied to either an arm or a thigh, and so several different cuff sizes would have to be carried.

A non-overlapping tourniquet is described by McEwen in U.S. Pat. No. 4,770,175. This cuff has a sliding clamp that secures the cuff snugly around the limb before inflation, and the excess length of the bladder hangs loose from the clamp. The bladder is inflated from the end of the excess bladder portion, and the clamp therefore allows air inside the bladder to pass through from the excess bladder portion into the bladder portion encircling the limb such that the full length of the bladder inflates; the cuff will not function if the clamp seals the bladder into separate sections. The inflated bladder portions on both sides of the clamp prevent the bladder from sliding through the clamp and therefore help maintain a fixed bladder circumference around the limb. However the additional inflated volume of the excess bladder length is a disadvantage in military and emergency situations, as described above. Furthermore, the clamp described in the '175 patent is intended to be applied by a skilled technician and is not adapted to single-handed operation; specifically the ends of the bladder are held in one hand and the clamp is slid down to the limb and closed using a second hand.

Pneumatic tourniquet cuffs require a source of pressurized gas to inflate the bladder, but the weight, bulk, and power requirements of surgical type pressure regulation and time monitoring systems (such as the pneumatic systems described by McEwen in U.S. Pat. No. 4,469,099) make them impractical for emergency self-use. Manual inflation means such as a hand pump or bulb (as shown with the overlapping pneumatic cuff tested by Calkins) is a practical alternative. However, even with manual inflation means, elapsed inflation time and cuff pressure should be monitored and indicated to the user to allow for minimization of the injuries and complications described in the opening paragraph. These monitoring and indicating functions ideally require minimal input from the user, who is likely under extreme stress while using the tourniquet.

There is no prior art pneumatic tourniquet for stopping arterial blood flow known to the inventors of the current invention which provides for self-application of the cuff with one hand, is suitable for a range of circumferences allowing application to the upper or lower limb, and inflates only in the region encircling the limb to which the cuff is applied. Furthermore there is no prior art pneumatic tourniquet cuff as described above known to the inventors of the current invention which also includes inflated time indication means automatically activated by manual pressurization of the tourniquet.

DETAILED DESCRIPTION OF THE PREFERRED EMBODIMENT

A specific embodiment illustrated is not intended to be exhaustive or to limit the invention to the precise form disclosed. It is chosen and described in order to explain the principles of the invention and its application and practical use, and thereby enable others skilled in the art to utilize the invention.

Throughout this document the terms 'bond' and 'bonded' will generally refer to processes such as radio frequency (RF) welding, ultrasonic sewing and welding, other forms of plastic welding, adhesive bonding, or solvent bonding selected to be suitable for the materials and coatings chosen for the various components of the cuff. Width and thickness of the bonds are selected to produce a joint of sufficient strength to withstand the stresses produced by typical cuff inflation pressures up to 1000 mmHg at various limb circumferences, and in selected areas, to form a gas impermeable joint between the materials. The terms 'seal' and 'sealed' refer specifically to gas-tight or gas impermeable joints forming an inflatable bladder.

Figure 1:
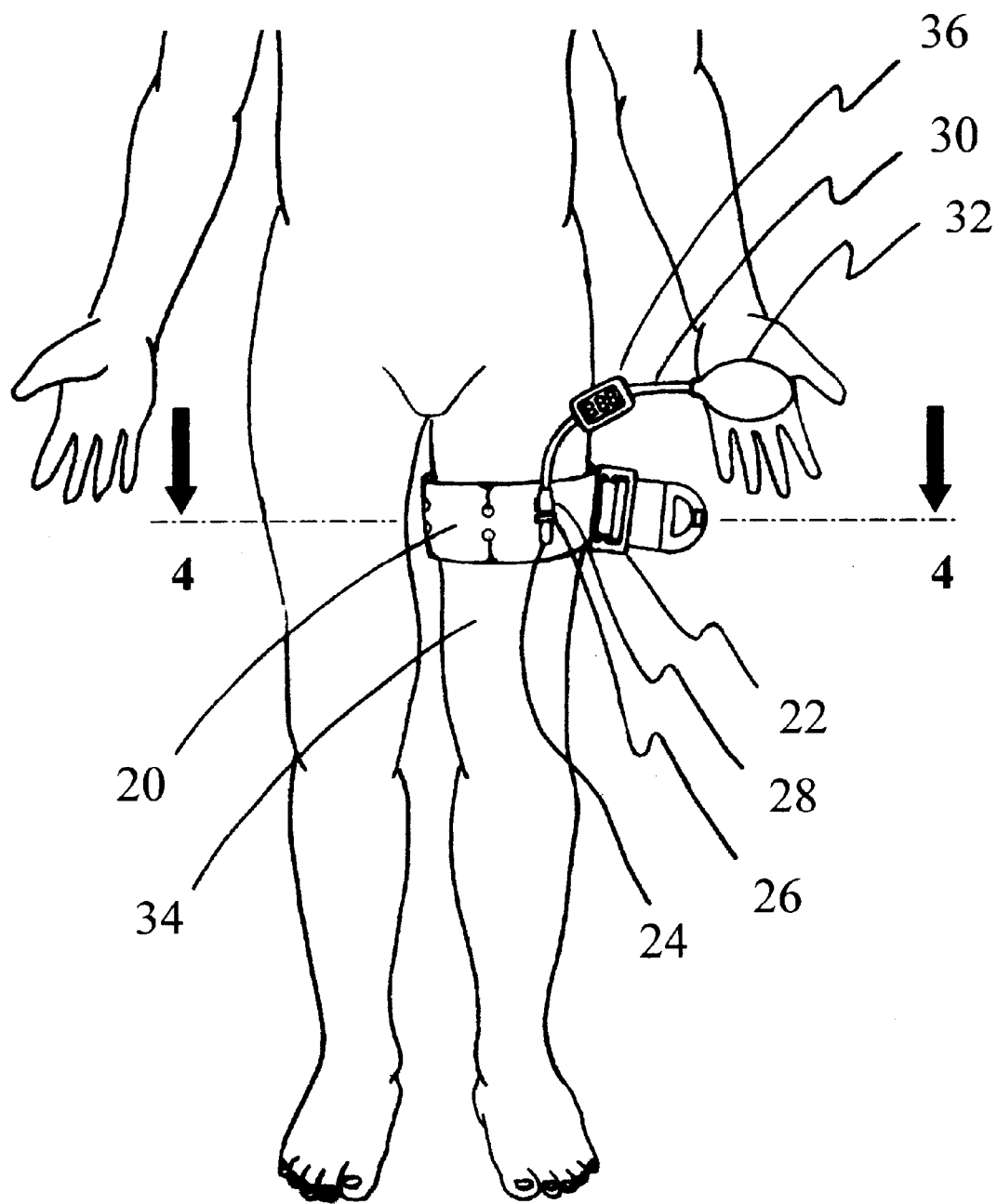
FIG. 1 is shows the tourniquet in use on a user's thigh.

FIG. 1 shows the preferred embodiment of the invention applied to a thigh. Cuff 20 is secured around limb 34 by clamp 22. Port 24, cuff connector 26, hose connector 28, and hose 30 form a gas-tight passageway between inflation bulb 32 and cuff 20. To apply cuff 20, the user passes the looped cuff 20 over the distal end of the injured limb 34, positions it proximal to the wound, then pulls cuff 20 snug around limb 34 and locks clamp 22. The user then manually inflates cuff 20 by squeezing inflation bulb 32 repeatedly until cuff 20 applies sufficient inward radial compression to the limb to prevent blood from flowing distally past cuff 20. It will be appreciated that cuff 20 may also be used to apply pressure to a dressing lying directly on the wound, in which case the inflation pressure required will be substantially less than that required to occlude arterial blood flow as described above.

Indicator module 36 (described in detail in FIG. 7) is connected pneumatically to the gas tight passageway in hose 30 and indicates cuff pressure and elapsed inflation time to the user of cuff 20. Indicator module 36 also operates to alert the user and provide instructions if predetermined alarm conditions are present.

Figure 2:
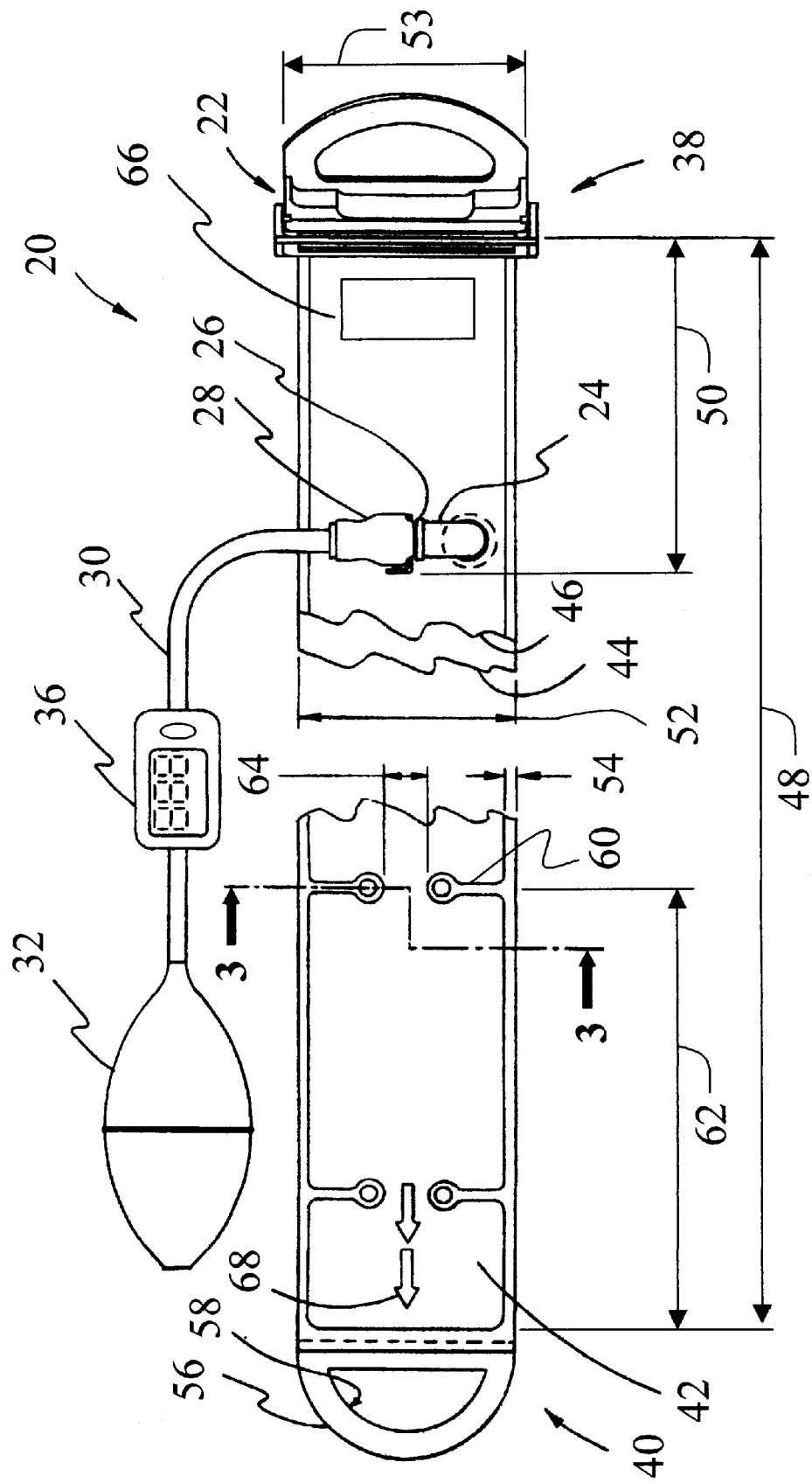
FIG. 2 is an overall view of the tourniquet.

FIG. 2 is an overall view of cuff 20 laid out flat. Cuff 20 has fixed end 38, sliding end 40, and bladder 42 having a length 48 selected to be sufficient for the bladder 42 to completely encircle the largest limb intended for cuff 20. Cuff 20 is constructed of inner layer 44 lying against the limb and outer layer 46 facing away from the limb, both made of gas impermeable material bonded together along a perimeter to form inflatable bladder 42. It will be appreciated inflatable bladder 42 may also be formed by bonding together inner layer 44 and outer layer 46 along their long edges and across fixed end 38 only, with the sealed perimeter closed by clamp 22 as shown in FIG. 4.

Figure 4:
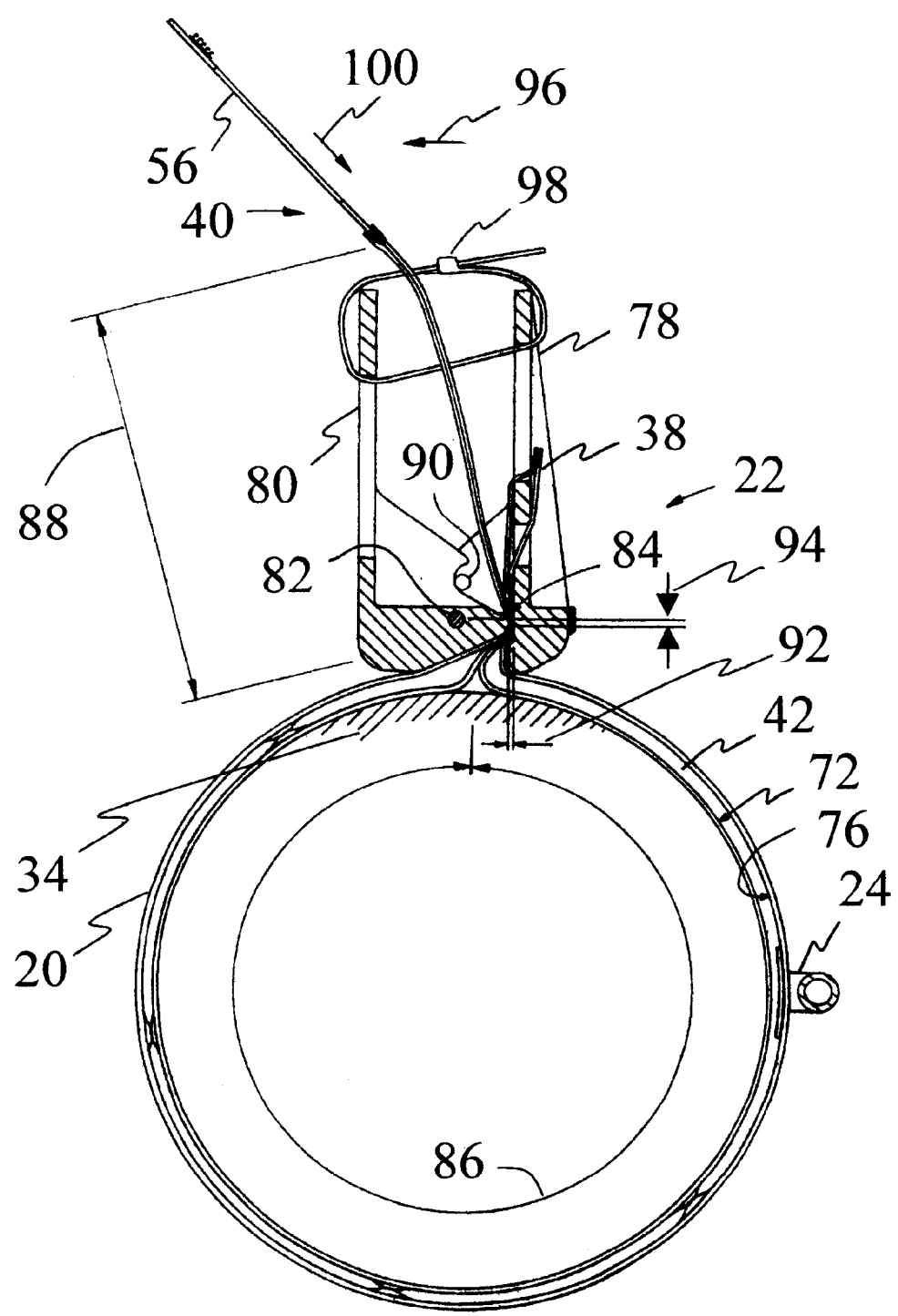
FIG. 4 is a section view through a limb with the tourniquet applied snug and inflated with the clamp in the locked position.
Figure 6:
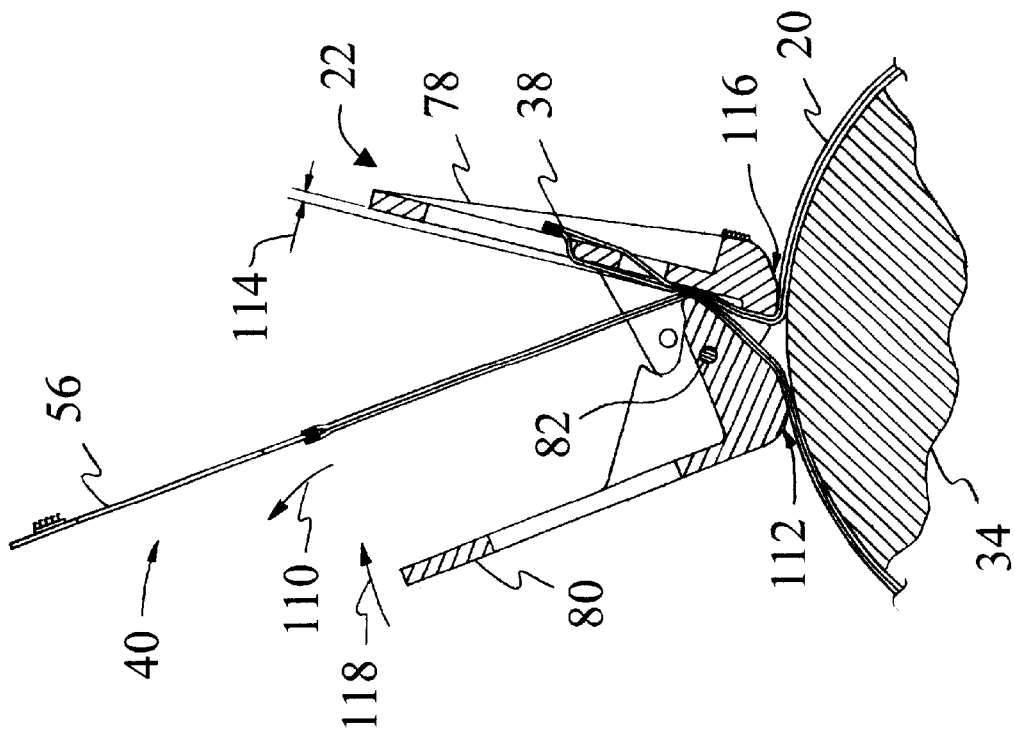
FIG. 6 is a detail section view through the tourniquet snug on the limb with the clamp in the intermediate position.
Figure 5:
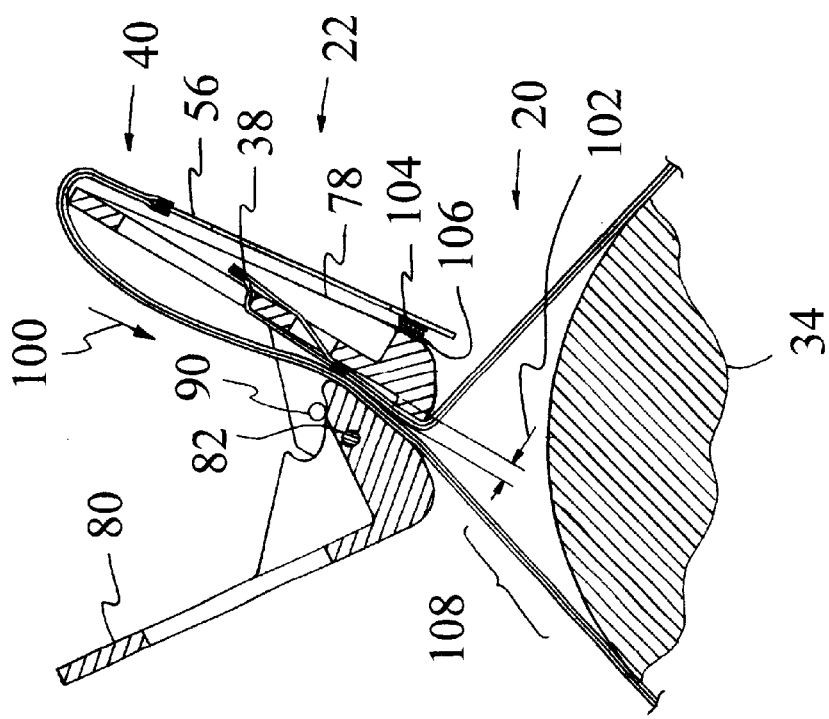
FIG. 5 is a detail section view through the tourniquet loose on the limb with the clamp in the open position.

For illustrative purposes cuff 20 is shown laid out flat with sliding end 40 unthreaded from clamp 22; in use sliding end 40 slides through clamp 22 as shown in FIGS. 4, 5, and 6. Thus the minimum limb circumference that cuff 20 can be used on is defined by distance 50, at which circumference port 24 prevents sliding end 40 from continuing through clamp 22. A suitable length 48 of bladder 42 is 34 inches and a suitable distance 50 is 5 inches. A suitable overall cuff width 52 is 3.5 inches, and bond width 54 is 0.20 inches. Clamp 22 is permanently attached to fixed end 38, and bladder 42 extends into clamp 22 as shown in detail in FIGS. 4, 5, and 6.

Clamp width 53 is selected to be larger than overall cuff width 52 to permit sliding end 40 to pass through clamp 22 at an angle relative to fixed end 38, thus allowing cuff 20 to assume a conical shape when wrapped around a conical limb (such as a typical thigh). This is important in achieving a snug fit around limbs of various degrees of conical shape, thereby reducing the pressure and inflated volume required to stop arterial blood flow in the limb.

At sliding end 40, pull tab 56 is bonded to cuff 20. Pull tab 56 is made of thin, stiff sheet material such as 0.020 thick polyurethane, durometer 75D, and is cut out along edge 58 to allow the user's thumb or finger to pass through and pull on sliding end 40 to tighten cuff 20 around the limb.

To prevent cuff 20 from rolling down the limb when inflated (particularly when used on a conical limb), inner layer 44 and outer layer 46 are further bonded together at flute 60. A plurality of flutes 60 are located at selected distances along bladder 42 and prevent expansion of bladder 42 in the region of each flute 60. A suitable flute spacing 62 is 5 inches and a suitable gap 64 is 0.625 inches. Expansion of bladder 42 is controlled in the area of each flute 60, eliminating the need for a stiffener as used in typical surgical pneumatic tourniquet cuffs. Fluted bladder designs are further described by McEwen in U.S. Pat. Nos. 5,312,431 and 5,584,853 which are hereby incorporated by reference.

Port 24 is permanently bonded to outer layer 46 and includes cuff connector 26 (PMC2202, Colder Products Company, St. Paul Minn.). Hose connector 28 (PMC1702, Colder Products Company, St. Paul Minn.) is permanently attached to hose 30, which in turn is permanently attached to indicator module 36 and inflation bulb 32, thereby providing a gas tight passageway from inflation bulb 32 to bladder 42 with a releasable connection at connectors 26 and 28. If the victim is transferred to a more sophisticated care setting where a conventional surgical tourniquet system (such as that described by McEwen in U.S. Pat. No. 4,469,099) is available, connectors 26 and 28 allow cuff 20 to be connected to the system without removal of cuff 20. Connectors 26 and 28 are a positive locking design (as described by McEwen in U.S. Pat. No. 5,649,954) which produce an audible click sound when fully engaged and locked, and allow hose 30 to rotate about its cylindrical axis relative to cuff 20 without unlocking or affecting the pneumatic connection.

Instructions 66 and symbols 68 are permanently marked on outer layer 46 to aid the user in applying cuff 20.

Figure 3:
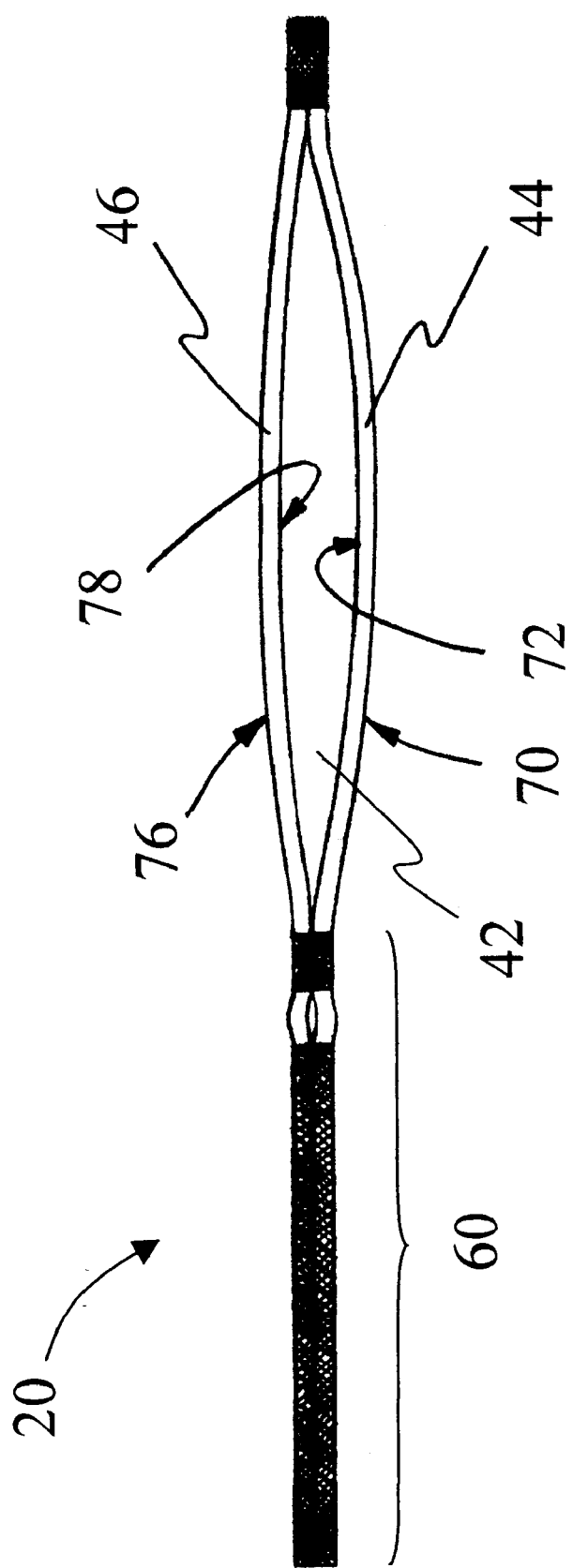
FIG. 3 is cross sectional view through the tourniquet showing a flute.

FIG. 3 is cross sectional view through cuff 20 in the region of bladder 42 passing through flute 60 at one side edge of cuff 20 and through an area between flutes 60 on the opposite side edge of cuff 20. Inner layer 44 is made of 70 denier woven nylon material with inner surface 70 against the limb and bladder surface 72 coated with a gas impermeable layer of thermoplastic. Smoothness of inner surface 70 is selected to allow cuff 20 to slide against the limb surface as cuff 20 is pulled tight, allowing clamp 22 (shown in FIG. 4) to remain accessible, while not being slippery enough to allow the cuff to slide distally on the limb upon inflation when the cuff and limb are wet. Outer layer 46 is made of 200 denier woven nylon material with a matte, brushed finish on outer surface 76 and coated on bladder surface 78 with a gas impermeable layer of thermoplastic. A suitable thermoplastic layer for both inner layer 44 and outer layer 46 is 0.006 inch thick polyurethane. Outer surface 76 has a selected color to suit the application, such as black for military applications or bright orange for emergency applications. The color of inner surface 70 may be chosen to be different from the color of outer surface 76 to help prevent the user from applying cuff 20 inside out or twisted. To further help prevent application error, symbols may be printed on inner surface 70 indicating that the surface must lie against the limb.

For military and emergency applications where cuff 20 may be carried by the user or is part of a compact kit of supplies carried by a medic, it is particularly important that the packed size and overall weight of cuff 20 be minimized. Accordingly the materials for inner and outer layers 44 and 46 are selected to be flexible so that cuff 20 can be easily rolled or folded into a small package, and lightweight. In contrast, many conventional surgical tourniquets have a stiffener within or lying against the bladder, hook or loop type fasteners attached along most of the bladder length, and hook or loop type straps extending beyond a bladder end, all of which prevent compact rolling or folding of the cuff and increase weight.

It will be appreciated that a variety of materials and thermoplastics may be chosen for various applications of the invention; for example non-woven fabrics and polyvinylchloride (PVC) thermoplastic may be used if a less costly, less durable version of the invention is desired.

It will also be appreciated that to further simplify manufacture, cuff 20 could also be formed out of a gas impermeable tube material (such as 0.025 inch thick 73 durometer flexible PVC) cut to the overall cuff length with a gas-tight bond formed across fixed end 36 (shown in FIG. 2).

FIG. 4 is a section view through limb 34 with cuff 20 applied and inflated and clamp 22 in the locked position. Also visible are port 24 and pull tab 56. Application of cuff 20 and operation of clamp 22 are shown in detail in FIGS. 5 and 6. Base 78 and rocker 80 are joined by pivot pin 82 and are free to rotate relative to each other about pivot pin 82. When clamp 22 is in the locked position as shown, the circumference of cuff 20 is fixed and bladder 42 is sealed across its entire width at sealing ridge 84, thereby creating inflating portion 86 in contact with the limb and non-inflating portion 88. Upon inflation, inflating portion 86 expands and, due to its fixed circumference, inward radial pressure is applied to the limb. With sufficient inflation pressure, arterial blood flow in limb 34 distal to cuff 20 is stopped.

Sealing the bladder at clamp 22 ensures that the inflated volume is minimized for the particular limb cuff 20 is applied to; for example the length of cuff 20 must be sufficient to encircle most thighs, yet when applied to the typical arm approximately 60% of the length of bladder 20 is not required and not in contact with the limb. The sealing function of clamp 22 is therefore an important advantage minimizing the time and effort required to inflate the cuff and stop bleeding. This is particularly important in the battlefield or emergency situation when cuff 20 is self-applied by the injured person.

As clamp 22 is closed, rotation of rocker 80 relative to base 78 is stopped by stop pin 90 striking rocker 80. Gap 92 between base 78 and sealing ridge 84 is selected to be less than the uncompressed total thickness of the fixed end 38 and the sliding end 40 of cuff 20. Therefore in the locked position the thermoplastic layers on surfaces 72 and 76 are compressed and form an airtight seal against each other. Fixed end 38 passes through gap 92 to provide two additional layers of compressible material underneath sealing ridge 84, thereby improving the reliability of the seal between inflating portion 86 and non-inflating portion 88. Because bladder 42 is compressed against itself underneath sealing ridge 84, inflating portion 86 completely encircles the limb and has a length substantially equivalent to the limb circumference.

To further improve clamping and sealing functions of clamp 22, in the locked position the center of area of sealing ridge 84 lies over-center distance 94 from the line lying perpendicular to base 78 and passing through the center of pivot pin 82, thereby forming an over-center lock in which forces resulting from the compression of cuff 20 in gap 92 act to hold rocker 80 in the locked position. Circumferential tension in cuff 20 resulting from inflation also acts to hold clamp 22 in the locked position due to friction in gap 92 acting on rocker 80 in the direction of arrow 100. An appropriate gap 92 is 0.015 inches and an appropriate over-center distance 94 is 0.030 inches.

When clamp 22 is in the locked position, inflating portion 86 encircles the entire circumference of the limb, and the lengths of inflating portion 86 and non-inflating portion 88 vary depending on the circumference of the limb. This is an important distinction from blood pressure cuffs in the prior art (for example the cuff described by Ruff in U.S. Pat. No. 4,727,885), which typically have an inflating portion of fixed length and substantially shorter than the maximum limb circumference intended for the cuff. In these blood pressure cuffs the inflating portion must be positioned over a particular artery and the cuff is not intended to occlude all blood flow in the limb.

Inflating portion 86 does not overlap itself, as is typical in occlusive cuffs of the prior art with fixed length, overlapping bladders (for example cuffs described by McEwen in U.S. Pat. Nos. 5,649,954 and 5,741,295).

To unlock clamp 22, rocker 80 must be rotated relative to base 78 in the direction of arrow 96. Due to the over-center distance 94, maximum compression of cuff 20 under sealing ridge 84 occurs when rocker 80 is rotated in the direction of arrow 96 to a position where over-center distance 94 is reduced to zero. Therefore the force required to open clamp 22 from the locked position increases slightly as rocker 80 is rotated in the direction of arrow 96, reducing the chance of accidental unlocking.

Secondary locking means is provided by tie strap 98 joining rocker 80 and base 78 and may be applied by the user or other personnel in situations where clamp 22 may be accidentally be opened, such a dragging of the injured person over rough terrain.

FIG. 5 is a detail section view through cuff 20, clamp 22, and limb 34 similar to FIG. 4, but prior to tightening and inflating cuff 20 and with clamp 22 in the open position. Fixed end 38 of cuff 20 passes through gap 102 between base 78 and rocker 80 and is permanently attached to base 78. Sliding end 40 passes though gap 102 and is folded over base 78 and retained in the folded over position by hook fastener 104 permanently attached pull tab 56, and corresponding loop fastener 106 permanently attached to base 78. Cuff 20 is packaged in the configuration shown in FIG. 5 and thus forms a loop ready to be tightened around the limb. Referring also to FIGS. 1 and 4, upon unpacking the user passes the looped cuff 20 over the distal end of the injured limb, slides it to a position proximal to the bleeding wound, and pulls on pull tab 56, releasing hook and loop fasteners 104 and 106 and pulling sliding end 40 radially away from the limb (as seen in FIG. 6). Gap 102 is sufficient to allow sliding end 40 to pass through clamp 22 easily until cuff 20 is snugly applied to the limb. The opening angle formed as rocker 80 pivots relative to base 78 about pivot pin 82 is limited by stop pin 90, thereby ensuring that even when fully opened, clamp 22 may be grasped and locked as described in FIG. 4 with one hand.

In the event that it is impossible to pass the looped cuff 20 over the distal end of the injured limb, the user may release hook and loop fasteners 104 and 106, pull sliding end 40 out of clamp 22 in the direction of arrow 100, wrap the unlooped cuff around the limb, rethread sliding end 40 through gap 102, and tighten cuff 20 as described above. Pull tab 56 is of selected stiffness greater than that of inner and outer layers 44 and 46 and thereby provides a thin, stiff edge allowing sliding end 40 to be more easily passed through gap 102. Hook and loop fasteners 104 and 106 prevent accidental unthreading of sliding end 40 from clamp 22 if, for example, the user pulls on region 108 of cuff 20 during unpacking or application.

FIG. 6 is a detail section view through cuff 20 pulled snug around limb 34 with clamp 22 in the intermediate position. Snugness can be increased by pulling sliding end 40 in the direction of arrow 110, creating a pulley effect around rocker 80. However because the inward radial pressure on the limb is provided by inflation pressure in inflating portion 86 (shown in FIG. 4), cuff 20 need only be snug enough around limb 34 to lie closely against the surface of limb 34 and to remain in position until inflation is completed. At the typical snugness required, cuff 20 does not normally apply enough pressure to occlude venous blood flow (typically 20 mmHg). In contrast to prior art non-pneumatic strap type tourniquets which generate sufficient pressure to stop arterial blood flow through cinching up the strap portion encircling the limb to a high tension level (as described in the background), cuff 20 is easier to apply and there is less tendency for soft tissue and clothing underlying cuff 20 to be pinched or drawn into clamp 22 as cuff 20 is made snug around the limb.

As cuff 20 becomes snug around the limb, ridge 112 of rocker 80 contacts the limb. The position of ridge 112 relative to pivot pin 82 is selected such that the resulting force from the limb acting on ridge 112 creates a torque acting to turn rocker 80 relative to base 78 such that gap 114 is reduced. Furthermore, edge 116 of base 78 is positioned relative to pivot pin 82 such that contact with limb 34, along with the increasing snugness of cuff 20 acting on base 78 at fixed end 38, applies a torque acting to turn base 78 relative to rocker 80 such that gap 114 is reduced. Sufficient snugness of cuff 20 causes gap 114 to reduce to a point where sliding end 40 is held against fixed end 38 with sufficient force to prevent sliding end 40 from passing back through clamp 22 in a direction opposite to arrow 110 (thereby loosening the cuff) if pull tab 56 is released by the user. In this intermediate position of clamp 22, the user may release pull tab 56 after applying the cuff and use the same hand to lock clamp 22 as described below, allowing the user to apply cuff 20 with one hand.

To lock clamp 22 and thereby secure cuff 20 around the limb, the user squeezes pivot 80 towards base 78 in the direction of arrow 118 as far as possible, putting clamp 22 in the locked position shown in FIG. 4. As clamp 22 moves from the open position shown in FIG. 5 to the intermediate position shown in FIG. 6 and finally the locked position shown in FIG. 4, the distance between ridge 112 on rocker 80 and edge 116 on base 78 increases, so there is no tendency for clamp 22 to pinch the underlying soft tissues or to gather up underlying clothing as cuff 20 is made snug around the limb and secured.

Figure 7:
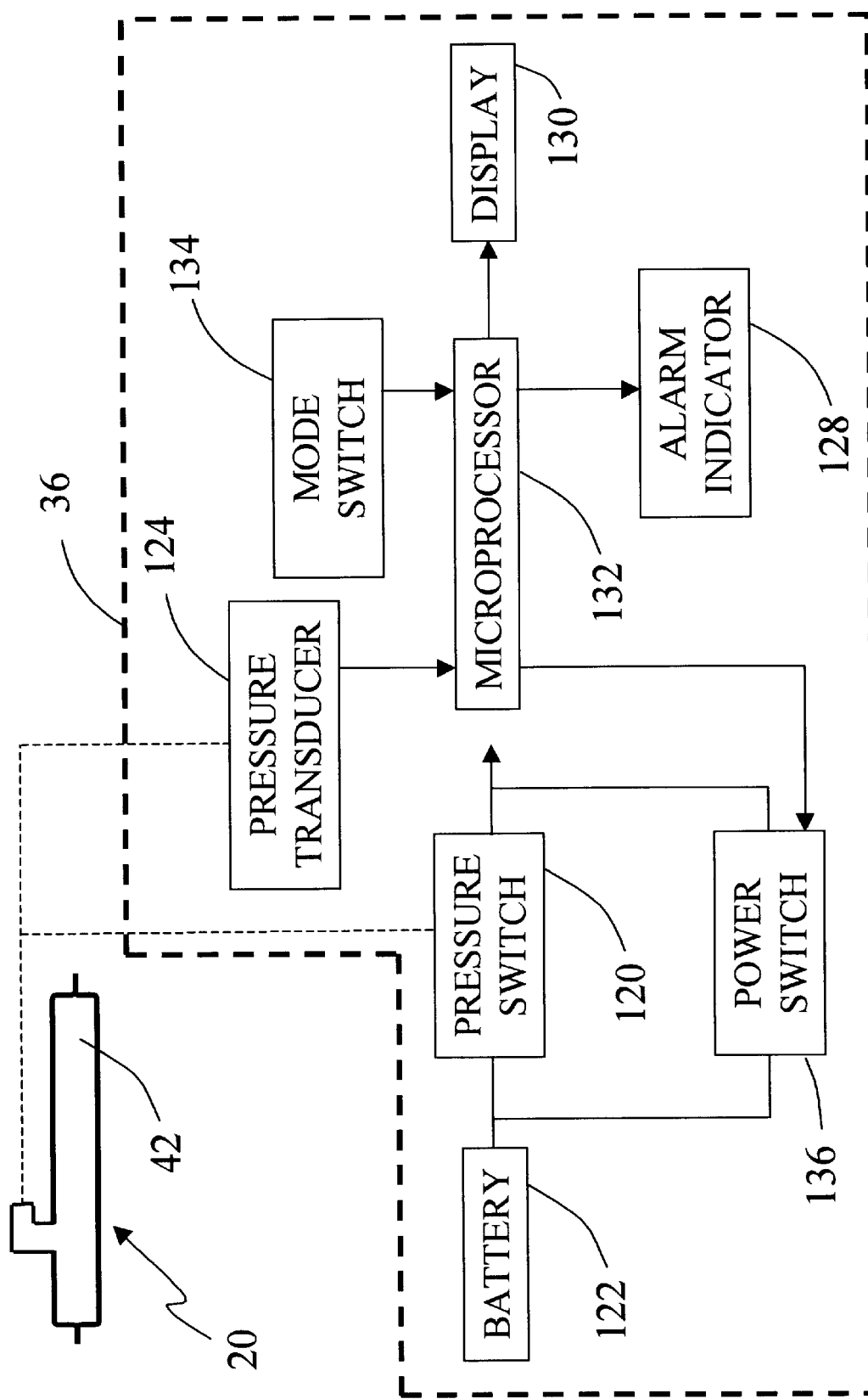
FIG. 7 is a block diagram of the indicator module.

FIG. 7 is a block diagram of indicator module 36 connected to cuff 20. Indicator module 36 operates as described below to indicate cuff pressure (the pressure of gas in bladder 42) and elapsed inflation time (the duration of time that the cuff pressure has exceeded a predetermined pressure threshold) to the user of cuff 20. Indicator module 36 also operates to alert the user and provide instructions if predetermined alarm conditions are present. As shown in FIG. 7 indicator module 36 consists of battery 122, pressure switch 120, power switch 136, pressure transducer 124, microprocessor 132, mode switch 134, display 130 and alarm indicator 128.

Pressure switch 120 communicates pneumatically with bladder 42 and closes when the pressure in bladder 42 increases to a predetermined threshold pressure indicating that cuff 20 is in use and is being inflated. In the preferred embodiment the predetermined threshold pressure that switch 120 closes at is 20 mmHg. Pressure switch 120 makes indicator module 36 easier to use by allowing indicator module 36 to automatically power up upon the inflation of bladder 42. Furthermore, power is drawn from battery 122 only when cuff 20 is in use, thereby preserving the life of battery 122 and allowing cuff 20 to be stored unused for long periods. When pressure switch 120 is closed, battery 122 supplies power to pressure transducer 124, alarm indicator 128, display 130, and microprocessor 132. Power switch 136 is connected in parallel with pressure switch 120 and is controlled by microprocessor 132. When activated by microprocessor 132, power switch 136 allows battery 122 to continue to supply power to pressure transducer 124, alarm indicator 128, display 130, and microprocessor 132.

When power is first applied to microprocessor 132 through the closure of pressure switch 120, microprocessor 132 activates power switch 136, this ensures that microprocessor 132 and related components will remain powered regardless of the pressure in bladder 42. Microprocessor 132 is programmed to deactivate power switch 136 when the pressure in bladder 42 has remained below a predetermined threshold pressure of 20 mmHg for a predetermined time interval of 60 minutes, thereby further conserving battery 122.

Pressure transducer 124 communicates pneumatically with bladder 42 and provides an indication of the pressure within bladder 42 to microprocessor 132. Microprocessor 132 is programmed to determine elapsed inflation time by measuring the duration of time that the pressure in bladder 42 has exceeded a predetermined pressure threshold, as indicated by pressure transducer 124.

Display 130 is controlled by microprocessor 132 to indicate cuff pressure, elapsed inflation time, and other instructions to the user. Mode switch 134 allows the user to select which of the monitored parameters, elapsed inflation time or cuff pressure is shown on display 130.

Alarm indicator 128 provides an audible and visual indication of alarm conditions to the user. Microprocessor 132 activates alarm indicator 128 under certain predetermined conditions of pressure and elapsed inflation time. For example, if the pressure in bladder 42 has been inflated above a predetermined threshold and has remained above this threshold continuously for a predetermined elapsed time interval, alarm indicator 128 is activated to warn the user to deflate cuff 20 for a reperfusion period of 5 to 10 minutes to reduce the extent of avoidable ischaemic damage to the limb. A suitable elapsed time interval is 2 hours, suggested by some in the surgical literature as a generally safe period for continuous occlusion in a limb. Alarm indicator 128 may also be activated by microprocessor 132 if unusually high pressures are detected in bladder 42 (for example pressures greater than 400 mmHg) to warn the user that the pressure may be higher than necessary and that the risk of limb injury has increased.

Microprocessor 132 may also be programmed to monitor rate of pressure change and activate alarm indicator 128 if a predetermined rate of pressure decline is exceeded, which may mean that cuff 20 is failing to maintain pressure due to damage or improper application.

Microprocessor 132 may also be programmed to monitor the difference between a reference pressure and the current pressure in bladder 42 and activate alarm indicator 128 if a predetermined difference is exceeded. For example the reference pressure may be indicated by the user via mode switch 134 when bladder 42 is inflated to sufficient pressure to stop bleeding, and alarm indicator 128 activated if the pressure in bladder 42 falls a predetermined amount below or rises a predetermined amount above the reference pressure, alerting the user to check for bleeding and adjust the inflation pressure if required. It is to be understood that the invention is not to be limited to the details herein given but may be modified within the scope of the appended claims.

We claim:

1. A pneumatic tourniquet adapted for self application by an injured person in a military or emergency situation to stop arterial blood loss in an injured arm or leg, comprising:

a bladder having a width dimension and having a length dimension greater than the circumference of an injured limb of a subject at a selected location; and clamp means for securing the bladder around the limb at the selected location and adapted for sealing the bladder across the bladder width to establish an inflatable portion of the bladder to be the portion of the bladder that encircles the injured limb at the selected location.

2. The tourniquet of claim 1 and including manual inflation means adapted to allow the inflatable portion of the bladder to be manually inflated to a pressure sufficient to stop arterial blood loss past the bladder.

3. The tourniquet of claim 1 wherein the clamp means further includes release means for allowing the subject to remove the secured bladder from the limb.

4. A pneumatic tourniquet adapted for self application by an injured person in a military or emergency situation to stop arterial blood loss in an injured arm or leg, comprising an inflatable bladder having a width dimension and having a length dimension greater than the circumference of an injured limb of a subject at a selected location;

clamp means for securing the bladder around the limb at the selected location so that the bladder remains secured around the limb while the bladder is inflated;

manual inflation means adapted to allow the bladder to be manually inflated to a pressure sufficient to stop arterial blood loss past the bladder; and timer means for indicating the duration of time the bladder has been pressurized above a predetermined pressure threshold wherein the timer is activated by the manual inflation of the bladder to a pressure greater than the predetermined pressure threshold.

5. The tourniquet of claim 4 wherein the clamp means further seals the bladder across the bladder width to form an inflatable bladder portion secured around the limb and having a bladder portion length substantially equivalent to the circumference of the injured limb at the selected location.

6. The tourniquet of claim 4 and including pressure indication means for providing an indication of the pressure to which the bladder is inflated.

7. A pneumatic tourniquet adapted for self application by an injured person in a military or emergency situation to stop arterial blood loss in an injured arm or leg, comprising:

an inflatable bladder having a first end, a second end and an overall length greater than a circumference of a limb of a subject at a predetermined location;

clamp means attached to the first end of the bladder and having an open position, an intermediate position and a locked position, wherein the open position is adapted to allow the subject to encircle the limb with the a portion of the bladder at the selected location and insert the second end of the bladder into the clamp means, wherein the intermediate position is adapted to allow the subject to reduce the circumference of the encircling portion of the bladder to be substantially equivalent to the circumference of the limb at the selected location, and wherein the locked position is adapted to allow the subject to secure the encircling portion of the bladder around the limb while the bladder is inflated.

8. The tourniquet of claim 7 including manual inflation means communicating pneumatically with the encircling portion of the bladder for enabling the subject to manually inflate the encircling portion of the bladder to a pressure sufficient to stop arterial blood flow past the encircling portion.

9. The tourniquet of claim 8 and including timer means for indicating the duration of time the bladder has been pressurized above a predetermined pressure threshold wherein the timer is activated by the manual inflation of the bladder to a pressure greater than the predetermined pressure threshold.

10. The tourniquet of claim 8 and including pressure indication means for providing an indication of the pressure to which the bladder is inflated.

11. The tourniquet of claim 7 wherein the inflatable bladder has a width dimension and the clamp means further seals the inflatable bladder across the width.

* * * * *